(12) United States Patent
Thomson et al.

(10) Patent No.: US 9,078,603 B2
(45) Date of Patent: Jul. 14, 2015

(54) SCANNING OPHTHALMOSCOPES

(75) Inventors: Martin Thomson, Lothian (GB); Derek Swan, Fife (GB); Daniel Gray, Fife (GB); Stephen Pemberton, Fife (GB)

(73) Assignee: OPTOS PLC, Dunfermline, Fife (GB)

( * ) Notice: Subject to any disclaimer, the term of this patent is extended or adjusted under 35 U.S.C. 154(b) by 267 days.

(21) Appl. No.: 13/642,986

(22) PCT Filed: Apr. 26, 2011

(86) PCT No.: PCT/GB2011/050818
§ 371 (c)(1),
(2), (4) Date: Dec. 12, 2012

(87) PCT Pub. No.: WO2011/135348
PCT Pub. Date: Nov. 3, 2011

(65) Prior Publication Data
US 2013/0093996 A1 Apr. 18, 2013

(30) Foreign Application Priority Data
Apr. 28, 2010 (GB) .................................. 1007046.4

(51) Int. Cl.
*A61B 3/14* (2006.01)
*A61B 3/00* (2006.01)
*A61B 3/13* (2006.01)
*A61B 3/10* (2006.01)

(52) U.S. Cl.
CPC .................. *A61B 3/13* (2013.01); *A61B 3/1025* (2013.01)

(58) Field of Classification Search
CPC ........ A61B 3/1025; A61B 3/102; A61B 3/12; A61B 3/14; A61B 2017/00694; A61B 3/1225; A61B 5/0073; A61B 3/0091; A61B 3/10; A61B 3/1015; A61B 3/1241; A61B 5/0059; A61B 2017/22087; A61B 3/0016
USPC ......... 351/200, 203, 205, 208, 206, 221, 222, 351/245, 246, 243
See application file for complete search history.

(56) References Cited

U.S. PATENT DOCUMENTS

| 5,798,823 A | 8/1998 | Kudo |
| 8,789,950 B2 * | 7/2014 | Mensink et al. ............... 351/221 |
| 2013/0135583 A1 * | 5/2013 | Gray et al. .................... 351/206 |

FOREIGN PATENT DOCUMENTS

| GB | 2440163 A | 1/2008 |
| WO | WO03/020121 A1 | 3/2003 |
| WO | WO2010/125394 A1 | 11/2010 |
| WO | WO2011/018644 A1 | 2/2011 |

* cited by examiner

*Primary Examiner* — Stephone B Allen
*Assistant Examiner* — Brandi Thomas
(74) *Attorney, Agent, or Firm* — Drinker Biddle & Reath LLP

(57) ABSTRACT

The present invention provides a scanning ophthalmoscope for scanning the retina of an eye and a method of scanning the retina of an eye. The ophthalmoscope (10) comprises a source of collimated light (12), a first scanning element (14), a second scanning element (16) and a scan relay device (18) having two foci (18a, 18b). The source of collimated light (12), the first and second scanning elements (14, 16) and the scan relay device (18) combine to provide a two-dimensional collimated light scan (21) from an apparent point source (19). The scanning ophthalmoscope (10) further comprises a scan transfer device (20), wherein the scan transfer device (20) has two foci (20a, 20b) and at least one vertex (20c) and the apparent point source (19) is provided at a first focus (20a) of the scan transfer device (20) and an eye (22) is accommodated at a second focus (20b) of the scan transfer device (20), and wherein the scan transfer device (20) transfers the two-dimensional collimated light scan (21) from the apparent point source (19) into the eye (22). The two foci (18a, 18b) of the scan relay device (18) and the two foci (20a, 20b) of the scan transfer device (20) define a first plane and the two foci (20a, 20b) and the at least one vertex (20c) of the scan transfer device (20) define a second plane and wherein the first and second planes are substantially parallel.

19 Claims, 3 Drawing Sheets

SCANNING OPHTHALMOSCOPES

The present invention relates to a scanning ophthalmoscope for scanning the retina of an eye and a method of scanning the retina of an eye.

An ultra-wide field scanning ophthalmoscope for scanning retinas is described in the Applicant's European Patent No. 0730428. The system comprises:
1. a slow scan element;
2. a fast scan element;
3. an ellipsoidal main mirror; and
4. a scan compensator.

The slow scan element provides a scanning motion of an incident laser beam, in a first direction. The fast scan element provides a scanning motion of the incident laser beam, in a second direction, orthogonal to the first direction.

The fast scan element is positioned at the first focus point of the ellipsoidal main mirror and the subject's pupil is positioned at the second focus point of the ellipsoidal main mirror. Therefore, light emanating from the first focus point of the mirror is reflected through the second focus point of the mirror, and therefore, through the subject's pupil.

As a result of the apparent or virtual point source, the system enables ultra-wide retinal images of the retina to be obtained. The system enables taking 120 degree external scans through 2 mm undilated pupils.

However, in order to allow transmission of the laser beam, it was found necessary to make modifications to the system described above. The modifications provided a lateral spacing between each of the above-referenced components, and applied a "tilt" to the input laser beam.

This modified system was found to work well, transferring light efficiently over the substantial scan angles. However, the consequence of the tilted input beam was that the scan on the retina had a "shear" component which varies as a function of field position. While this shear distortion does not affect the ability to diagnose pathology, it does impact initial perceptions and the ability to measure consistent dimensions within the retinal images.

According to a first aspect of the present invention there is provided a scanning ophthalmoscope for scanning the retina of an eye comprising:
 a source of collimated light;
 a first scanning element;
 a second scanning element;
 a scan relay device having two foci;
 wherein the source of collimated light, the first and second scanning elements and the scan relay device combine to provide a two-dimensional collimated light scan from an apparent point source; and
 the scanning ophthalmoscope further comprises a scan transfer device, wherein the scan transfer device has two foci and at least one vertex and the apparent point source is provided at a first focus of the scan transfer device and an eye is accommodated at a second focus of the scan transfer device, and wherein the scan transfer device transfers the two-dimensional collimated light scan from the apparent point source into the eye, and
 wherein the two foci of the scan relay device and the two foci of the scan transfer device define a first plane and the two foci and the at least one vertex of the scan transfer device define a second plane and wherein the first and second planes are substantially parallel.

The rotational axes of the first and second scanning elements are substantially orthogonal.

The rotational axis of the first scanning element may be substantially parallel to a line joining the two foci of the scan relay device and the rotational axis of the second scanning element may be substantially perpendicular to a line joining the two foci of the scan transfer device. In this arrangement the rotational axis of the first scanning element is substantially parallel to the first and second planes and the rotational axis of the second scanning element is substantially perpendicular to the first and second planes.

Alternatively, the rotational axis of the first scanning element may be substantially perpendicular to a line joining the two foci of the scan relay device and the rotational axis of the second scanning element may be substantially parallel to a line joining the two foci of the scan transfer device. In this arrangement the rotational axis of the first scanning element is substantially perpendicular to the first and second planes and the rotational axis of the second scanning element is substantially parallel to the first and second planes.

The rotational axis of the first scanning element may be within approximately 5° of the line joining the two foci of the scan relay device. The rotational axis of the first scanning element may be within approximately 2° of the line joining the two foci of the scan relay device. The rotational axis of the first scanning element and the line joining the two foci of the scan relay device, may have a degree of parallelism which depends on chosen eccentricities of one or more components of the scanning ophthalmoscope. The rotational axis of the first scanning element and the line joining the two foci of the scan relay device, may have a degree of parallelism determined by a user of the scanning ophthalmoscope, according to an acceptable level of shear in images of the retina produced by the ophthalmoscope.

The rotational axis of the second scanning element may be within approximately 5° of the line joining the two foci of the scan transfer device. The rotational axis of the second scanning element may be within approximately 2° of the line joining the two foci of the scan transfer device. The rotational axis of the second scanning element and the line joining the two foci of the scan transfer device, may have a degree of parallelism which depends on chosen eccentricities of one or more components of the scanning ophthalmoscope. The rotational axis of the second scanning element and the line joining the two foci of the scan transfer device, may have a degree of parallelism determined by a user of the scanning ophthalmoscope, according to an acceptable level of shear in images of the retina produced by the ophthalmoscope.

The scan relay device may comprise at least one vertex.

The scan relay device may comprise an elliptical mirror. The scan relay device may comprise an aspherical mirror. The scan relay device may comprise an ellipsoidal mirror. Where the scan relay device is one of the group comprising an elliptical mirror, an aspherical mirror or an ellipsoidal mirror, the scan relay device comprises one vertex.

The scan relay device may comprise a pair of parabola mirrors. The scan relay device may comprise a pair of paraboloidal mirrors. Where the scan relay device is pair of parabola mirrors or a pair of paraboloidal mirrors, the scan relay device comprises two vertices. In this arrangement the two vertices and the two foci of the scan relay device lie on the same plane.

The scan transfer device may comprise an elliptical mirror. The scan transfer device may comprise an aspherical mirror. The scan transfer device may comprise an ellipsoidal mirror. Where the scan transfer device is one of the group comprising an elliptical mirror, an aspherical mirror or an ellipsoidal mirror, the scan transfer device comprises one vertex.

The scan transfer device may comprise a pair of parabola mirrors. The scan transfer device may comprise a pair of paraboloidal mirrors. Where the scan transfer device is pair of parabola mirrors or a pair of paraboloidal mirrors, the scan transfer device comprises two vertices. In this arrangement the two vertices and the two foci of the scan transfer device lie on the same plane.

One foci of the scan relay device may be coincident with one foci of the scan transfer device. The second focus of the scan relay device may be coincident with the first focus of the scan transfer device.

The first scanning element may be positioned at the first focus point of the scan relay device and the second scanning element may be positioned at the second focus point of the scan relay device. In the arrangement where the second focus point of the scan relay device is coincident with the first focus of the scan transfer device, the second scanning element is also positioned at the first focus point of the scan transfer device.

The first scanning element may comprise a rotating mechanism. The first scanning element may comprise a rotating polygon mirror.

The first scanning element may comprise an oscillating mechanism.

The second scanning element may comprise an oscillating mechanism. The second scanning element may comprise an oscillating plane mirror.

The second scanning element may comprise a rotating mechanism. The second scanning element may comprise a rotating plane mirror.

The source of collimated light may comprise a laser light source. The source of collimated light may comprise a light emitting diode.

The scanning ophthalmoscope may be able to produce up to 150 degree scans, for example 120 degrees, 110 degrees, 90 degrees, 60 degrees, 40 degrees, of the retina of the eye, measured at the pupillary point of the eye. The scanning ophthalmoscope may be able to produce such scans of the retina of the eye, through a 2 mm undilated pupil of the eye.

The scanning ophthalmoscope may also comprise one or more light detectors for detecting reflected light from the retina in order to produce an image of the scanned area of the retina of the eye.

According to a second aspect of the present invention there is provided a method of scanning the retina of an eye comprising the steps of:
 providing a source of collimated light, a first scanning element, a second scanning element and a scan relay device, wherein the scan relay device has two foci;
 using the source of collimated light, the first and second scanning elements and the scan relay device in combination to provide a two-dimensional collimated light scan from an apparent point source;
 providing a scan transfer device having two foci and at least one vertex;
 providing the apparent point source at a first focus of the scan transfer device and accommodating the eye at the second focus of the scan transfer device;
 using the scan transfer device to transfer the two-dimensional collimated light scan from the apparent point source to the eye, and
 wherein the two foci of the scan relay device and the two foci of the scan transfer device define a first plane and the two foci and the at least one vertex of the scan transfer device define a second plane and the first and second planes are substantially parallel.

The first and second scanning elements are positioned such that their axes of rotation are substantially orthogonal.

The rotational axis of the first scanning element may be substantially parallel to a line joining the two foci of the scan relay device and the rotational axis of the second scanning element may be substantially perpendicular to a line joining the two foci of the scan transfer device. In this arrangement the rotational axis of the first scanning element is substantially parallel to the first and second planes and the rotational axis of the second scanning element is substantially perpendicular to the first and second planes.

Alternatively, the rotational axis of the first scanning element may be substantially perpendicular to a line joining the two foci of the scan relay device and the rotational axis of the second scanning element may be substantially parallel to a line joining the two foci of the scan transfer device. In this arrangement the rotational axis of the first scanning element is substantially perpendicular to the first and second planes and the rotational axis of the second scanning element is substantially parallel to the first and second planes.

The rotational axis of the first scanning element may be within approximately 5° of the line joining the two foci of the scan relay device. The rotational axis of the first scanning element may be within approximately 2° of the line joining the two foci of the scan relay device.

The rotational axis of the first scanning element and the line joining the two foci of the scan relay device, may have a degree of parallelism which depends on chosen eccentricities of one or more components of the scanning ophthalmoscope. The rotational axis of the first scanning element and the line joining the two foci of the scan relay device, may have a degree of parallelism determined by a user of the scanning ophthalmoscope, according to an acceptable level of shear in images of the retina produced by the ophthalmoscope.

The rotational axis of the second scanning element may be within approximately 5° of the line joining the two foci of the scan transfer device. The rotational axis of the second scanning element may be within approximately 2° of the line joining the two foci of the scan transfer device. The rotational axis of the second scanning element and the line joining the two foci of the scan transfer device, may have a degree of parallelism which depends on chosen eccentricities of one or more components of the scanning ophthalmoscope. The rotational axis of the second scanning element and the line joining the two foci of the scan transfer device, may have a degree of parallelism determined by a user of the scanning ophthalmoscope, according to an acceptable level of shear in images of the retina produced by the ophthalmoscope.

According to a third aspect of the present invention there is provided a scanning ophthalmoscope for scanning the retina of an eye comprising:
 a source of collimated light;
 a first scanning element;
 a second scanning element;
 a scan relay device;
 wherein the source of collimated light, the first and second scanning elements and the scan relay device combine to provide a two-dimensional collimated light scan from an apparent point source; and
 the scanning ophthalmoscope further comprises a scan transfer device, wherein the scan transfer device has two foci and the apparent point source is provided at a first focus of the scan transfer device and an eye is accommodated at a second focus of the scan transfer device, and wherein the scan transfer device transfers the two-dimensional collimated light scan from the apparent point source into the eye,
 wherein the rotational axis of the second scanning element is substantially perpendicular to a line joining the two foci of the scan transfer device, and
 wherein, in the provision of the two-dimensional collimated light scan from the apparent point source, the scan relay device produces a one-dimensional collimated light scan, and the line joining the two foci of the scan transfer device is substantially perpendicular to a plane defined by the one-dimensional collimated light scan produced by the scan relay device.

The rotational axis of the first scanning element may be substantially parallel to the line joining the two foci of the scan relay device. The rotational axis of the first scanning element may be substantially parallel to a plane defined by the two foci and the vertex of the scan transfer device. Similarly, the rotational axis of the first scanning element may be substantially parallel to a plane defined by the two foci and the vertex of the scan relay device.

The rotational axis of the first scanning element may be within approximately 5° of the line joining the two foci of the scan relay device. The rotational axis of the first scanning element may be within approximately 2° of the line joining the two foci of the scan relay device. The rotational axis of the first scanning element and the line joining the two foci of the scan relay device, may have a degree of parallelism which depends on chosen eccentricities of one or more components of the scanning ophthalmoscope. The rotational axis of the first scanning element and the line joining the two foci of the scan relay device, may have a degree of parallelism determined by a user of the scanning ophthalmoscope, according to an acceptable level of shear in images of the retina produced by the ophthalmoscope.

The scan relay device may comprise an elliptical mirror. The scan relay device may comprise an aspherical mirror. The scan relay device may comprise an ellipsoidal mirror. Where the scan relay device is one of the group comprising an elliptical mirror, an aspherical mirror or an ellipsoidal mirror, the scan relay device comprises one vertex.

The scan relay device may comprise a pair of parabola mirrors. The scan relay device may comprise a pair of paraboloidal mirrors. Where the scan relay device is a pair of parabola mirrors or a pair of paraboloidal mirrors, the scan relay device comprises two vertices. In this arrangement the two vertices and the two foci of the scan relay device lie on the same plane.

The scan transfer device may comprise an elliptical mirror. The scan transfer device may comprise an aspherical mirror. The scan transfer device may comprise an ellipsoidal mirror. Where the scan transfer device is one of the group comprising an elliptical mirror, an aspherical mirror or an ellipsoidal mirror, the scan relay device comprises one vertex.

The scan transfer device may comprise a pair of parabola mirrors. The scan transfer device may comprise a pair of paraboloidal mirrors. Where the scan transfer device is a pair of parabola mirrors or a pair of paraboloidal mirrors, the scan transfer device comprises two vertices. In this arrangement the two vertices and the two foci of the scan transfer device lie on the same plane.

The scan relay device may comprise two foci. One foci of the scan relay device may be coincident with one foci of the scan transfer device. The rotational axis of the first scanning element is substantially perpendicular to a line joining the two foci of the scan relay device.

The first scanning element may comprise a rotating mechanism. The first scanning element may comprise a rotating polygon mirror.

The first scanning element may comprise an oscillating mechanism.

The second scanning element may comprise an oscillating mechanism. The second scanning element may comprise an oscillating plane mirror.

The second scanning element may comprise a rotating mechanism. The second scanning element may comprise a rotating plane mirror.

The source of collimated light may comprise a laser light source. The source of collimated light may comprise a light emitting diode.

The scanning ophthalmoscope may be able to produce up to 150 degree scans, for example 120 degrees, 110 degrees, 90 degrees, 60 degrees, 40 degrees, of the retina of the eye, measured at the pupillary point of the eye. The scanning ophthalmoscope may be able to produce such scans of the retina of the eye, through a 2 mm undilated pupil of the eye.

According to a fourth aspect of the present invention there is provided a method of scanning the retina of an eye comprising the steps of:

providing a source of collimated light, a first scanning element, a second scanning element and a scan relay device;

using the source of collimated light, the first and second scanning elements and the scan relay device in combination to provide a two-dimensional collimated light scan from an apparent point source;

providing a scan transfer device having two foci;

positioning the second scanning element such that its rotational axis is substantially perpendicular to a line joining the two foci of the scan transfer device;

providing the apparent point source at a first focus of the scan transfer device and accommodating the eye at the second focus of the scan transfer device;

using the scan transfer device to transfer the two-dimensional collimated light scan from the apparent point source to the eye, wherein in the provision of the two-dimensional collimated light scan from the apparent point source, the scan relay device produces a one-dimensional collimated light scan, and the line joining the two foci of the scan transfer device is substantially perpendicular to a plane defined by the one-dimensional collimated light scan produced by the scan relay device.

Embodiments of the present invention will now be described, by way of example only, with reference to the accompanying drawing, in which.

The scanning ophthalmoscope is able to produce 120 degree scans, measured at the pupillary point, through 2 mm undilated pupils. Other scan angles are also possible.

Figure 1:
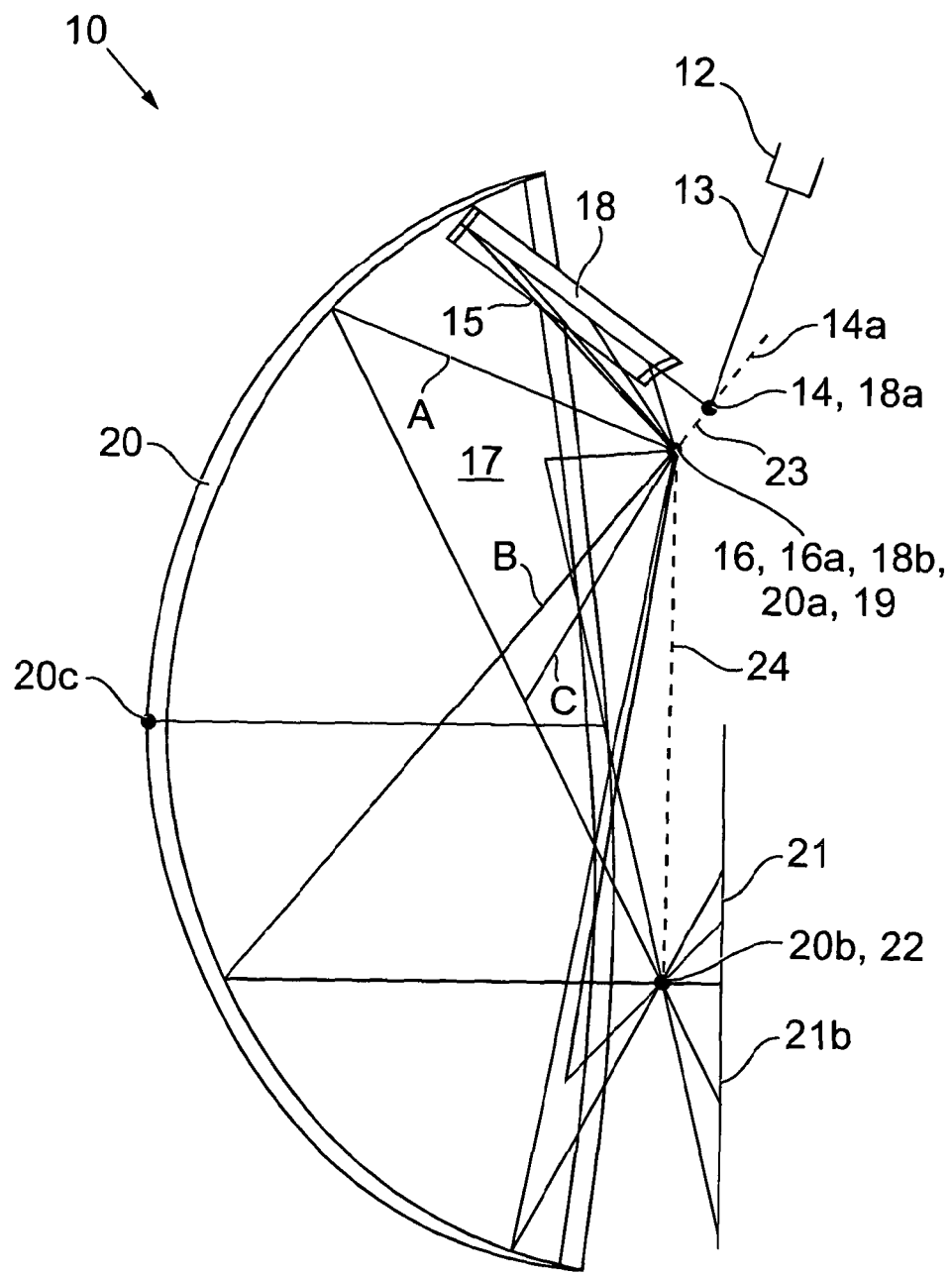
FIG. 1 is an optical schematic side view of a scan relay device and scan transfer device of a scanning ophthalmoscope according to the present invention, which indicates the incident path from a source of collimated light to a subject's eye.
Figure 2:
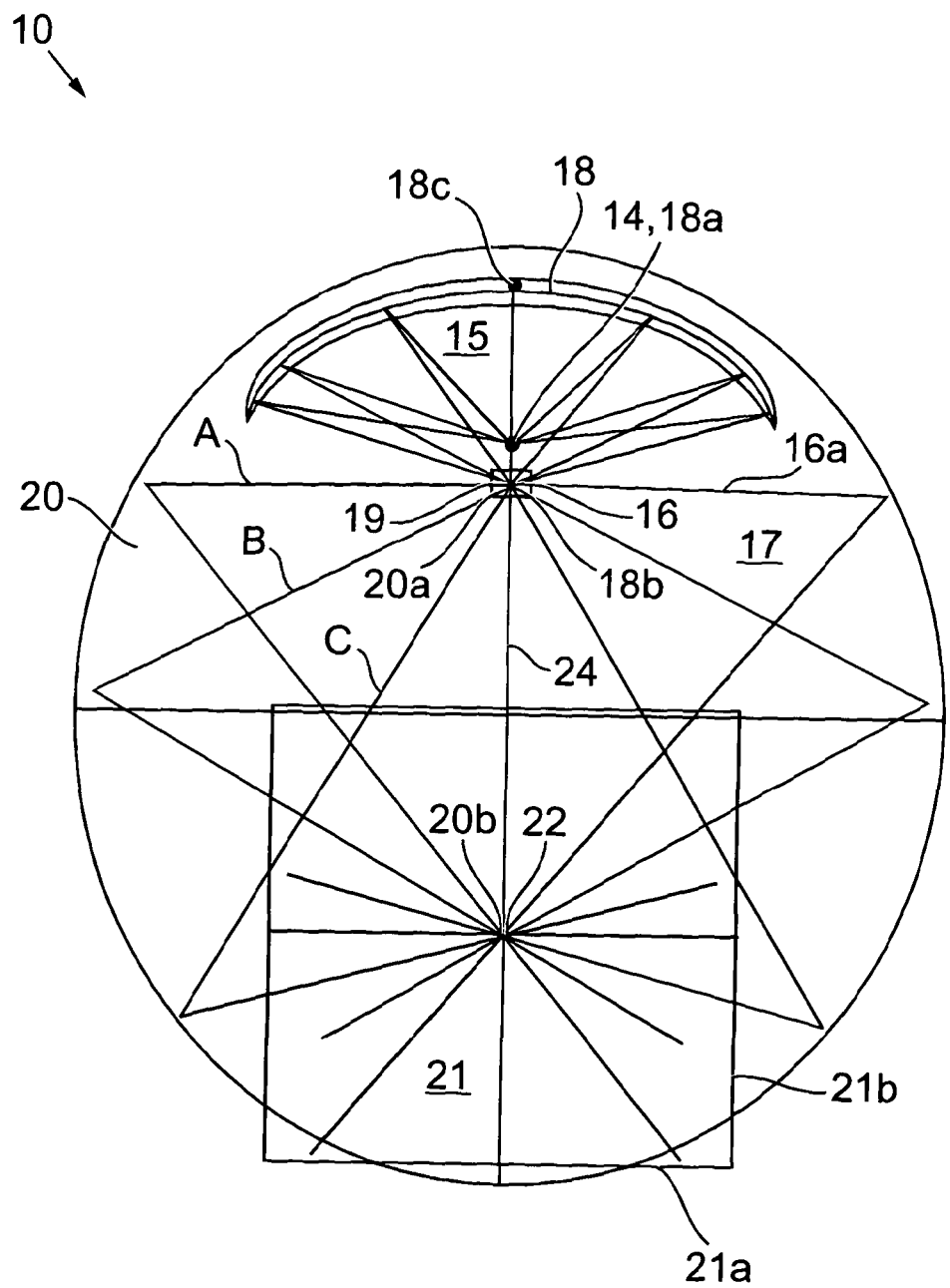
FIG. 2 is a front view of FIG. 1.

With reference to FIGS. 1 and 2, the scanning ophthalmoscope 10 comprises a source of collimated light which is a laser 12 producing a laser beam 13, a first scanning element 14, a second scanning element 16, a scan relay device 18 and a scan transfer device 20. Note that the source of collimated light 12 and the laser beam 13 has been omitted from FIG. 2 for clarity.

The first scanning element 14 is a high speed rotating polygon mirror and the second scanning element 16 is a slow speed oscillating plane mirror. The first scanning element 14 has an axis of rotation 14a and the second scanning element 16 has an axis of rotation 16a. The axes of rotation 14a, 16a of the first and second scanning elements 14, 16 are substantially orthogonal. The rotational axis 14a of the first scanning element 14 is substantially parallel to a line 23 joining the two foci 18a, 18b of the scan relay device 18 (see below). The rotational axis 16a of the second scanning element 16 is substantially perpendicular to a line 24 joining the two foci 20a, 20b of the scan transfer device 20 (see below).

The polygon mirror 14 and the oscillating plane mirror 16 are arranged to create a two-dimensional collimated light scan, in the form of a raster scan pattern 21 (see FIG. 2) of the laser beam 13. The polygon mirror 14 has a plurality of facets, and provides a plurality of first one-dimensional collimated light scans, which, in this embodiment of the invention, comprises horizontal one-dimensional scans 21a of the laser beam 13. For each polygon mirror rotation, each facet of the polygon mirror 14 generates a horizontal scan component 21a of the raster scan pattern 21.

FIG. 2 best illustrates the path of the laser beam 13 in a horizontal one-dimensional scan 15 produced by one facet of the polygon mirror 14, as this facet is rotated.

The oscillating plane mirror 16 provides a second one-dimensional collimated light scan 17, which, in this embodiment of the invention, comprises a vertical one-dimensional scan 21b of the laser beam 13. This generates a vertical scan component 21b of the raster scan pattern 21. Path A is an example of the laser beam 13 reflected from the oscillating plane mirror 16 at the start of the oscillation; path B is an example of the laser beam 13 reflected from the oscillating plane mirror 16 at an intermediate point of the oscillation; and path C is an example of the laser beam 13 reflected from the oscillating plane mirror 16 at the end of the oscillation.

The polygon mirror 14 and the oscillating plane mirror 16 thus together create a two-dimensional collimated light scan in the form of the raster scan pattern 21, as illustrated in FIG. 2.

The scan relay device 18 has two foci 18a, 18b and a vertex 18c. In the embodiment described here the scan relay device 18 is an ellipsoidal mirror, and is referred to as a slit mirror. It should be appreciated, however, that the scan relay device 18 may have an alternative form. The polygon mirror 14 is positioned at a first focus 18a of the slit mirror 18 and the oscillating plane mirror 16 is positioned at the second focus 18b of the slit mirror 18.

The scan transfer device 20 is an aspherical mirror in the form of an ellipsoidal mirror, and is referred to as a main mirror. The main mirror 20 has two foci 20a, 20b and a vertex 20c. The oscillating plane mirror 16 is also positioned at the first focus 20a of the main mirror 20. In this arrangement the second focus point 18b of the slit mirror 18 is coincident with the first focus 20a of the main mirror 20. A subject's eye 22 is positioned at a second focus 20b of the main mirror 20.

The laser beam 13 is thus conveyed to the subject's eye 22 and onto the retina (not shown), via the polygon mirror 14, the slit mirror 18, the oscillating plane mirror 16 and the main mirror 20.

The polygon mirror 14, the slit mirror 18, and the oscillating plane mirror 16, combine to provide a two-dimensional collimated light scan, in the form of a raster scan pattern 21, from an apparent point source 19. By virtue of the fact that the main mirror 20 has two foci 20a, 20b, the two-dimensional collimated light scan is coupled from the oscillating plane mirror 16 (first focus point 20a) to the subject's eye 22 (second focus point 20b).

The two foci 18a, 18b of the slit mirror 18 and the two foci 20a, 20b of the main mirror 20 define a first plane and the two foci 20a, 20b and vertex 20c of the main mirror 20 define a second plane. The first and second planes are substantially parallel. The rotational axis 14a of the first scanning element 14 is substantially parallel to the first and second planes and the rotational axis 16a of the second scanning element 16 is substantially perpendicular to the first and second planes. Although it should be appreciated that the rotational axis 14a of the first scanning element 14 and the rotational axis 16a of the second scanning element 16 could be switched such that the rotational axis 14a of the first scanning element 14 is substantially perpendicular to the first and second planes and the rotational axis 16a of the second scanning element 16 is substantially parallel to the first and second planes. In such an alternative arrangement the surface of the slit mirror 18 would need to be expanded to facilitate vertical scanning of the laser beam 13.

The plane defined by the two foci 18a, 18b and vertex 18c of the slit mirror 18 is also substantially parallel to the plane defined by the two foci 20a, 20b and vertex 20c of the main mirror 20 (second plane).

A beam reflected from the retina of the subject's eye 22 is conveyed back through the scanning ophthalmoscope 10, and is used to produce an image of the subject's retina. The scanning ophthalmoscope 10 also comprises a number of light detectors (not shown) for detecting reflected light from the retina in order to produce an image of the scanned area of the retina of the eye.

The scan relay device 18 serves a number of functions within the scanning ophthalmoscope 10.

A first function of the scan relay device 18 is that of scan transfer of the laser beam 13 from the polygon mirror 14 to the oscillating plane mirror 16. As a result of the scan relay device 18 having two focus points 18a, 18b, the scan relay device 18 provides point to point transfer, without introducing any translational component, which would cause failure of the laser beam 13 to enter through the pupil of the subject's eye. Thus the laser beam 13 appears to come from an apparent point source 19.

Since the polygon mirror 14 is positioned at the first focus 18a of the slit mirror 18, light from the polygon mirror 14 will always be reflected through the second focus 18b of the slit mirror 18, regardless of the angle of deflection of light from the polygon mirror 14 onto the slit mirror 18. The effect of this is that the raster scan pattern 21 of the laser beam 13 is transmitted without disruption through the pupil of the subject's eye 22. This enables ultra-wide retinal images of the retina to be obtained.

A second function of the scan relay device 18 is that of a scan angle amplifier. An inherent problem with ultra-wide field laser scanning ophthalmoscopes is the difficulty in achieving rapid deflection of the laser beam when creating the raster scan pattern over the required angular range. The element normally used to produce the "fast" part of the raster scan pattern is typically a rotating polygon mirror. For example, a 6-sided polygon mirror can clearly generate 120 degree optical scans. However, if the scan is to be sufficiently fast for acceptable image acquisition rates, the polygon mirror needs to rotate at extremely high speeds. This requires impractically high performance from a polygon mirror scanning system.

In order to create scans of the order of 120 degrees, a polygon mirror with 16 facets may be used. Each facet rotation produces 22.5 degrees of "mechanical" scan and 45 degrees of "optical" scan. Such a polygon mirror can be used with a scan relay device which provides scan angle amplification. This system allows the rotational speed of the polygon mirror to be reduced, whilst still creating a wide angle raster scan pattern at an acceptable rate.

In the embodiment of the present invention, the polygon mirror 14 comprises 16 facets. Each facet produces a one-dimensional scan of the laser beam 13, comprising a "fan" of laser light rays. These rays travel to the slit mirror 18. The rays are then brought to focus at the oscillating plane mirror 16. According to the eccentricity of the slit mirror 18, there can be scan angle amplification. For example, in order to achieve scan angles of the order of 120 degrees, the scan angle amplification provided by the slit mirror 18 should be approximately three times the input angle, i.e. approximately 3×45 degrees.

A third function of the scan relay device 18 is that it also shapes the laser beam 13, providing static pre-compensation of aberrations introduced by the main mirror 20. This improves the resolution of the retinal images produced by the scanning ophthalmoscope 10. Further, when the scan relay device 18 is an ellipsoidal mirror, astigmatisms can be reduced without necessitating a further cylindrical lens.

Figure 3:
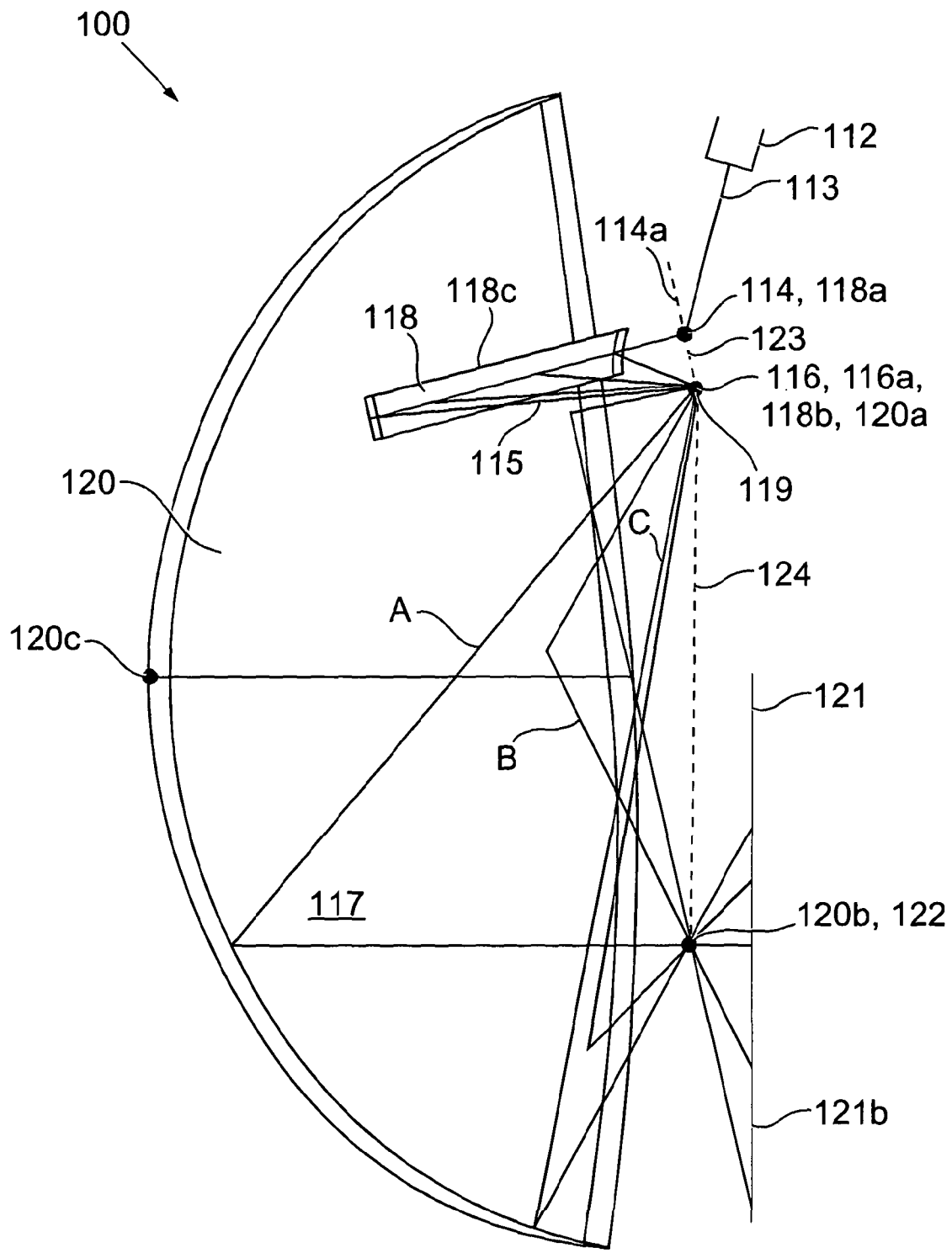
FIG. 3 is an optical schematic side view of a scan relay device and scan transfer device of a scanning ophthalmoscope according to an alternate embodiment of the present invention, which indicates the incident path from a source of collimated light to a subject's eye.

FIG. 3 illustrates an alternative embodiment of the scanning ophthalmoscope 10. The only difference between this embodiment and the first embodiment is the positional relationship between the slit mirror 18 and the main mirror 20, all other components and operations remain unchanged.

The scanning ophthalmoscope 100 is able to produce 120 degree scans, measured at the pupillary point, through 2 mm undilated pupils. Other scan angles are also possible.

With reference to FIG. 3, the scanning ophthalmoscope 100 comprises a source of collimated light which is a laser 112 producing a laser beam 113, a first scanning element 114, a second scanning element 116, a scan relay device 118 and a scan transfer device 120.

The first scanning element 114 is a high speed rotating polygon mirror and the second scanning element 116 is a slow speed oscillating plane mirror. The first scanning element 114 has an axis of rotation 114a and the second scanning element 116 has an axis of rotation 116a. The axes of rotation 114a, 116a of the first and second scanning elements 114, 116 are substantially orthogonal. The rotational axis 114a of the first scanning element 114 is substantially parallel to a line 123 joining the two foci 118a, 118b of the scan relay device 118 (see below). The rotational axis 116a of the second scanning element 116 is substantially perpendicular to a line 124 joining the two foci 120a, 120b of the scan transfer device 120 (see below).

The polygon mirror 114 and the oscillating plane mirror 116 are arranged to create a two-dimensional collimated light scan, in the form of a raster scan pattern 121 of the laser beam 113. The polygon mirror 114 has a plurality of facets, and provides a plurality of first one-dimensional collimated light scans, which, in this embodiment of the invention, comprises horizontal one-dimensional scans 121a of the laser beam 113. For each polygon mirror rotation, each facet of the polygon mirror 114 generates a horizontal scan component 121 a of the raster scan pattern 121.

FIG. 3 illustrates the path of the laser beam 113 in a horizontal one-dimensional scan 115 produced by one facet of the polygon mirror 114, as this facet is rotated.

The oscillating plane mirror 116 provides a second one-dimensional collimated light scan 117, which, in this embodiment of the invention, comprises a vertical one-dimensional scan 121b of the laser beam 13. This generates a vertical scan component 121b of the raster scan pattern 121. Path A is an example of the laser beam reflected from the oscillating plane mirror 116 at the start of the oscillation; path B is an example of the laser beam reflected from the oscillating plane mirror 116 at an intermediate point of the oscillation; and path C is an example of the laser beam reflected from the oscillating plane mirror 116 at the end of the oscillation.

The polygon mirror 114 and the oscillating plane mirror 116 thus together create a two-dimensional collimated light scan in the form of the raster scan pattern 121.

The scan relay device 118 has two foci 118a, 118b and a vertex 118c. In the embodiment described here the scan relay device 118 is an ellipsoidal mirror, and is referred to as a slit mirror. It should be appreciated, however, that the scan relay device 118 may have an alternative form. The polygon mirror 114 is positioned at a first focus 118a of the slit mirror 118 and the oscillating plane mirror 116 is positioned at the second focus 118b of the slit mirror 118.

The scan transfer device 120 is an aspherical mirror in the form of an ellipsoidal mirror, and is referred to as a main mirror. The main mirror 120 has two foci 120a, 120b and a vertex 120c. The oscillating plane mirror 116 is also positioned at a first focus 120a of the main mirror 210. In this arrangement the second focus point 118b of the slit mirror 118 is coincident with the first focus 120a of the main mirror 120. A subject's eye 122 is positioned at a second focus 120b of the main mirror 120.

The laser beam 113 is thus conveyed to the subject's eye 122, via the polygon mirror 114, the slit mirror 118, the oscillating plane mirror 116 and the main mirror 120. The polygon mirror 114, the slit mirror 118, and the oscillating plane mirror 116, combine to provide a two-dimensional collimated light scan, in the form of a raster scan pattern 121, from an apparent point source 119. By virtue of the fact that the main mirror 120 has two foci 120a, 120b, the two-dimensional collimated light scan is coupled from the oscillating plane mirror 116 (first focus point 120a) to the subject's eye 122 (second focus point 120a).

The two foci 118a, 118b of the slit mirror 118 and the two foci 120a, 120b of the main mirror 120 define a first plane and the two foci 120a, 120b and vertex 120c of the main mirror 120 define a second plane. However, in the embodiment described here, the first and second planes do not necessarily need to be substantially parallel. The rotational axis 114a of the first scanning element 114 is substantially parallel to the first and second planes and the rotational axis 116a of the second scanning element 116 is substantially perpendicular to the first and second planes. A beam reflected from the retina of the subject's eye 122 is conveyed back through the scanning ophthalmoscope 100, and is used to produce an image of the subject's retina. The scanning ophthalmoscope 100 also comprises a number of light detectors (not shown) for detecting reflected light from the retina in order to produced an image of the scanned area of the retina of the eye.

The scan relay device 118 serves a number of functions within the scanning ophthalmoscope 100.

A first function of the scan relay device 118 is that of scan transfer of the laser beam 113 from the polygon mirror 114 to the oscillating plane mirror 116. The scan relay device 118 provides point to point transfer, without introducing any translational component, which would cause failure of the laser beam 113 to enter through the pupil of the subject's eye. Thus the laser beam 113 appears to come from an apparent point source 119.

Since the polygon mirror 114 is positioned at the first focus of the slit mirror 118, light from the polygon mirror 114 will always be reflected through the second focus of the slit mirror 118, regardless of the angle of deflection of light from the polygon mirror 114 onto the slit mirror 118. The effect of this is that the raster scan pattern 121 of the laser beam 113 is transmitted without disruption through the pupil of the subject's eye 122. This enables ultra-wide retinal images of the retina to be obtained.

A second function of the scan relay device 118 is that of a scan angle amplifier. An inherent problem with ultra-wide field laser scanning ophthalmoscopes is the difficulty in achieving rapid deflection of the laser beam when creating the raster scan pattern over the required angular range. The element normally used to produce the "fast" part of the raster scan pattern is typically a rotating polygon mirror. For example, a 6-sided polygon mirror can clearly generate 120 degree optical scans. However, if the scan is to be sufficiently fast for acceptable image acquisition rates, the polygon mirror needs to rotate at extremely high speeds. This requires impractically high performance from a polygon mirror scanning system.

In order to create scans of the order of 120 degrees, a polygon mirror with 16 facets may be used. Each facet rotation produces 22.5 degrees of "mechanical" scan and 45 degrees of "optical" scan. Such a polygon mirror can be used with a scan relay device which provides scan angle amplification. This system allows the rotational speed of the polygon mirror to be reduced, whilst still creating a wide angle raster scan pattern at an acceptable rate.

In the embodiment of the present invention, the polygon mirror 114 comprises 16 facets. Each facet produces a one-dimensional scan of the laser beam 113, comprising a "fan" of laser light rays. These rays travel to the slit mirror 118. The rays are then brought to focus at the oscillating plane mirror 116. According to the eccentricity of the slit mirror 118, there can be scan angle amplification. For example, in order to achieve scan angles of the order of 120 degrees, the scan angle amplification provided by the slit mirror 118 should be approximately three times the input angle, i.e. approximately 3×45 degrees.

A third function of the scan relay device 118 is that it also shapes the laser beam 113, providing static pre-compensation of aberrations introduced by the main mirror 120. This improves the resolution of the retinal images produced by the scanning ophthalmoscope 100. Further, when the slit mirror 118 is an ellipsoidal mirror, astigmatisms can be reduced without necessitating a further cylindrical lens.

The components of the scanning ophthalmoscope 100 are arranged such that the rotational axis 116a of the oscillating plane mirror 116 is substantially perpendicular to the line 124 joining the two foci 120a, 120b of the main mirror 120. Furthermore, in the provision of the two-dimensional collimated light scan from the apparent point source 119, the polygon mirror 114 produces a one-dimensional scan 115 which is incident on the slit mirror 18. The slit mirror 118 also therefore produces a one-dimensional scan 115a. The components of the scanning ophthalmoscope 100 are arranged such that the line 124 joining the two foci 120a, 120b of the main mirror 120 is substantially perpendicular to a plane defined by the one-dimensional scan 115a produced by the slit mirror 118.

As described above, the components of the scanning ophthalmoscope 10 (first embodiment, FIGS. 1 and 2) are arranged such that the two foci 18a, 18b of the scan relay device 18 and the two foci 20a, 20b of the scan transfer device 20 lie on a first plane and the two foci 20a, 20b and the vertex 20c of the scan transfer device 20 lie on a second plane which is parallel to the first plane and the components of the scanning ophthalmoscope 100 (second embodiment, FIG. 3) are arranged such that the rotational axis 116a of the oscillating plane mirror 116 is substantially perpendicular to the line 124 joining the two foci 120a, 120b of the main mirror 120 and the line 124 joining the two foci 120a, 120b of the main mirror 120 is substantially perpendicular to a plane defined by the one-dimensional scan 115a produced by the slit mirror 118. Both of these arrangements provided images free from shear, or images with reduced shear, by removing the requirement to provide a tilt to the input laser beam 13, 113.

With reference to FIGS. 1 and 2, it should be appreciated that the relative positions of the sit mirror 18 and the main mirror 20 may be changed without affecting the operation of the ophthalmoscope 10, provided that the first and second planes remain substantially parallel. For example, with reference to FIG. 1, the slit mirror 18 could be rotated about its second focus point 18a (first focus point 20a of the main mirror 20) without affecting the operation of the ophthalmoscope 10, provided that the first and second planes remain substantially parallel.

With reference to FIG. 3, it should also be appreciated that the relative positions of the sit mirror 118 and the main mirror 120 may be changed without affecting the operation of the ophthalmoscope 100, provided that the line 124 joining the two foci 120a, 120b of the main mirror 120 is substantially perpendicular to a plane defined by the one-dimensional scan 115a produced by the slit mirror 118. For example, the slit mirror 118 could be rotated about its second focus point 118a (first focus point 120a of the main mirror 120) without affecting the operation of the ophthalmoscope 100, provided that the line 124 joining the two foci 120a, 120b of the main mirror 120 remains substantially perpendicular to a plane defined by the one-dimensional scan 115a produced by the slit mirror 118.

These arrangements offer a number of advantages.

The key advantage of the above-described arrangement of components of both ophthalmoscopes 10, 100 is that the scanned image of the subject's retina does not have, or has a reduced, "shear" component. This is because the arrangement of the components of the scanning ophthalmoscope 10, 100 removes the requirement to provide a "tilt" to the input laser beam 13, thus improving orthogonality between the horizontal and vertical components 21a, 21b, 121a, 121b of the two-dimensional scan 21, 121 and the line 24, 124 joining the two foci 20a, 20b, 120a, 120b of the main mirror 20 120.

Therefore, it is possible to measure consistent dimensions within retinal images, thus facilitating simpler quantification of feature size within these images.

Another advantage of the arrangement of the components of the scanning ophthalmoscope 10, 100 of the present invention is that it is possible to control the amount of scan angle amplification provided by the slit mirror 18, 118. This may be done by selecting an appropriate portion of the slit mirror 18, 118 to scan the laser beam 13, 113 from the polygon mirror 14, 114 across.

Selecting an appropriate portion of the slit mirror 18, 118 may be done by varying the angle of incidence of the laser beam 13, 113 on the polygon mirror 14, 114, or by rotating the slit mirror 18, 118 relative to the main mirror 20, 120. For example, FIG. 1 illustrates the situation where the two foci of the slit mirror 18 are rotationally offset from the two foci of the main mirror 20, i.e. the polygon mirror 14 is not collinear with the two foci of the main mirror 20. Varying the amount of rotation of the slit mirror 18 affects the portion of the slit mirror 18 that is used and the scan angle amplification which is obtained. Therefore, the scan angle amplification can be controlled. The required number of facets on the polygon mirror 14 may then be selected accordingly. This provides a certain level of flexibility as regards the polygon mirror 14.

It is also possible to vary the scan angle amplification by using a slit mirror with an appropriate eccentricity.

Another advantage is that the number of components comprised in the scanning ophthalmoscope of the present invention may be reduced, in comparison to previous ophthalmoscopes. This increases the optical brightness of the ophthalmoscope of the present invention, which is important when obtaining retinal images.

A further advantage of the arrangements of the components of the scanning ophthalmoscope 10, 100 of the present invention is that active focal correction may be included very easily to produce improved off axis aberration performance. The "fast scan" is along the "low" aberration axes of the ellipsoidal mirrors and the slow scan is along the relatively higher aberration axes of the ellipsoidal mirrors. This makes the inclusion of active focal correction simpler.

The separate arrangements of the ophthalmoscopes 10, 100 of the present invention remove the requirement to provide a "tilt" to the input laser beam, thus improving orthogonality between the horizontal and vertical components of the two-dimensional scan and the line joining the two foci of the main mirror.

Modifications and improvements may be made to the above-described scanning ophthalmoscope without departing from the scope of the present invention. For example, although the scan relay device has been described above as being an ellipsoidal mirror having two foci, it should be appreciated that the scan relay device could take other forms. For example, the scan relay device could comprise an elliptical mirror, a pair of parabolic mirrors, a pair of paraboloidal mirrors or a combination of any of these components. The common technical feature provided by any of these component arrangements is that the scan relay device comprises two foci and produces a one-dimensional collimated light scan.

Where elliptical components are used in the scan relay device, it may also be necessary to provide beam compensation elements, such as cylindrical lenses.

Furthermore, although the above described arrangement of the scanning ophthalmoscope has the polygon mirror positioned at the first focus of the slit mirror and the oscillating plane mirror located at the second focus of the slit mirror, it should be appreciated that the position of the polygon mirror and the oscillating plane mirror may be switched without affecting the operation of the ophthalmoscope.

Also, although the second scanning element has been described above as an oscillating plane mirror, it should be appreciated that this could be a rotating plane mirror.

In addition, although the above embodiment of the present invention has been described as providing 120 degree optical scans, it should be appreciated that the ophthalmoscope 10 may be configured to provide a lesser or greater angle of optical scan. As described above, this may be achieved, for example, by varying selection of the portion of the slit mirror that the laser beam is scanned across.

Also, although the source of collimated light has been described above as being a laser, it should be appreciated that the source of collimated light could be a light emitting diode.

Furthermore, although in the description of the ophthalmoscope 10 described above and illustrated in FIGS. 1 and 2 the rotational axis of the first scanning element has been described as being substantially parallel to the line joining the two foci of the scan relay device and the rotational axis of the second scanning element has been described as being substantially perpendicular to the line joining the two foci of the scan transfer device, it should be appreciated that the rotational axis of the first scanning element may be substantially perpendicular to the line joining the two foci of the scan relay device and the rotational axis of the second scanning element may be substantially parallel to the line joining the two foci of the scan transfer device without affecting the operation. In this arrangement the rotational axis of the first scanning element is substantially perpendicular to the first and second planes and the rotational axis of the second scanning element is substantially parallel to the first and second planes.

The invention claimed is:

1. A scanning ophthalmoscope for scanning the retina of an eye comprising:
    a source of collimated light;
    a first scanning element;
    a second scanning element;
    a scan relay device having two foci;
    wherein the source of collimated light, the first and second scanning elements and the scan relay device combine to provide a two-dimensional collimated light scan from an apparent point source; and
    the scanning ophthalmoscope further comprises a scan transfer device, wherein the scan transfer device has two foci and at least one vertex and the apparent point source is provided at a first focus of the scan transfer device and an eye is accommodated at a second focus of the scan transfer device, and wherein the scan transfer device transfers the two-dimensional collimated light scan from the apparent point source into the eye, and
    wherein the two foci of the scan relay device and the two foci of the scan transfer device define a first plane and the two foci and the at least one vertex of the scan transfer device define a second plane and wherein the first and second planes are substantially parallel.

2. A scanning ophthalmoscope according to claim 1, wherein the rotational axis of the first scanning element is substantially parallel to a line joining the two foci of the scan relay device and the rotational axis of the second scanning element is substantially perpendicular to a line joining the two foci of the scan transfer device.

3. A scanning ophthalmoscope according to claim 1, wherein the rotational axis of the first scanning element is substantially perpendicular to a line joining the two foci of the scan relay device and the rotational axis of the second scanning element is substantially parallel to a line joining the two foci of the scan transfer device.

4. A scanning ophthalmoscope according to claim 1, wherein the scan relay device includes at least one vertex and the at least one vertex and the two foci of the scan relay device lie on the same plane.

5. A scanning ophthalmoscope according to claim 1, wherein the scan transfer device includes at least one vertex and the at least one vertex and the two foci of the scan transfer device lie on the same plane.

6. A scanning ophthalmoscope according to claim 1, wherein
    the scan relay device includes at least one vertex and the at least one vertex and the two foci of the scan relay device lie on the same plane;
    the scan transfer device includes at least one vertex and the at least one vertex and the two foci of the scan transfer device lie on the same plane; and
    the plane defined by the at least one vertex and the two foci of the scan relay device and the plane defined by the at least one vertex and the two foci of the scan transfer device are substantially parallel.

7. A method of scanning the retina of an eye comprising the steps of:
    providing a source of collimated light, a first scanning element, a second scanning element and a scan relay device, wherein the scan relay device has two foci;

using the source of collimated light, the first and second scanning elements and the scan relay device in combination to provide a two-dimensional collimated light scan from an apparent point source;

providing a scan transfer device having two foci and at least one vertex;

providing the apparent point source at a first focus of the scan transfer device and accommodating the eye at the second focus of the scan transfer device;

using the scan transfer device to transfer the two-dimensional collimated light scan from the apparent point source to the eye, and wherein the two foci of the scan relay device and the two foci of the scan transfer device define a first plane and the two foci and the at least one vertex of the scan transfer device define a second plane and the first and second planes are substantially parallel.

8. A method of scanning the retina of an eye according to claim 7, wherein the rotational axis of the first scanning element is substantially parallel to a line joining the two foci of the scan relay device and the rotational axis of the second scanning element is substantially perpendicular to a line joining the two foci of the scan transfer device.

9. A method of scanning the retina of an eye according to claim 7, wherein the rotational axis of the first scanning element is substantially perpendicular to a line joining the two foci of the scan relay device and the rotational axis of the second scanning element is substantially parallel to a line joining the two foci of the scan transfer device.

10. A scanning ophthalmoscope for scanning the retina of an eye comprising:
a source of collimated light;
a first scanning element;
a second scanning element;
a scan relay device;
wherein the source of collimated light, the first and second scanning elements and the scan relay device combine to provide a two-dimensional collimated light scan from an apparent point source; and
the scanning ophthalmoscope further comprises a scan transfer device, wherein the scan transfer device has two foci and the apparent point source is provided at a first focus of the scan transfer device and an eye is accommodated at a second focus of the scan transfer device, and wherein the scan transfer device transfers the two-dimensional collimated light scan from the apparent point source into the eye,
wherein the rotational axis of the second scanning element is substantially perpendicular to a line joining the two foci of the scan transfer device, and
wherein, in the provision of the two-dimensional collimated light scan from the apparent point source, the scan relay device produces a one-dimensional collimated light scan, and the line joining the two foci of the scan transfer device is substantially perpendicular to a plane defined by the one-dimensional collimated light scan produced by the scan relay device.

11. A scanning ophthalmoscope according to claim 10, wherein the rotational axis of the first scanning element is substantially parallel to a plane defined by the foci and a vertex of the scan transfer device.

12. A scanning ophthalmoscope according to claim 10, wherein the rotational axis of the first scanning element is substantially parallel to a line joining two foci of the scan relay device and the rotational axis of the second scanning element is substantially perpendicular to a line joining the two foci of the scan transfer device.

13. A scanning ophthalmoscope according to claim 10, wherein the rotational axis of the first scanning element is substantially perpendicular to a line joining two foci of the scan relay device and the rotational axis of the second scanning element is substantially parallel to a line joining the two foci of the scan transfer device.

14. A scanning ophthalmoscope according to claim 10, wherein the scan relay device includes at least one vertex and the at least one vertex and the two foci of the scan relay device line on the same plane.

15. A scanning ophthalmoscope according to claim 10, wherein the scan transfer device includes at least one vertex and the at least one vertex and the two foci of the scan transfer device line on the same plane.

16. A scanning ophthalmoscope according to claim 10, wherein the plane defined by the at least one vertex and the two foci of the scan relay device and the plane defined by the at least one vertex and the two foci of the scan transfer device are substantially parallel.

17. A method of scanning the retina of an eye comprising the steps of:
providing a source of collimated light, a first scanning element, a second scanning element and a scan relay device;
using the source of collimated light, the first and second scanning elements and the scan relay device in combination to provide a two-dimensional collimated light scan from an apparent point source;
providing a scan transfer device having two foci;
positioning the second scanning element such that its rotational axis is substantially perpendicular to a line joining the two foci of the scan transfer device;
providing the apparent point source at a first focus of the scan transfer device and accommodating the eye at the second focus of the scan transfer device;
using the scan transfer device to transfer the two-dimensional collimated light scan from the apparent point source to the eye,
wherein in the provision of the two-dimensional collimated light scan from the apparent point source, the scan relay device produces a one-dimensional collimated light scan, and the line joining the two foci of the scan transfer device is substantially perpendicular to a plane defined by the one-dimensional collimated light scan produced by the scan relay device.

18. A method of scanning the retina of an eye according to claim 17, wherein the rotational axis of the first scanning element is substantially parallel to a line joining the two foci of the scan relay device and the rotational axis of the second scanning element is substantially perpendicular to a line joining the two foci of the scan transfer device.

19. A method of scanning the retina of an eye according to claim 17, wherein the rotational axis of the first scanning element is substantially perpendicular to a line joining the two foci of the scan relay device and the rotational axis of the second scanning element is substantially parallel to a line joining the two foci of the scan transfer device.

* * * * *